United States Patent [19]

Claytor et al.

[11] Patent Number: 4,542,644
[45] Date of Patent: Sep. 24, 1985

[54] VOID/PARTICULATE DETECTOR

[75] Inventors: Thomas N. Claytor, Woodridge; Henry B. Karplus, Hinsdale, both of Ill.

[73] Assignee: The United States of America as represented by the United States Department of Energy, Washington, D.C.

[21] Appl. No.: 535,979

[22] Filed: Sep. 26, 1983

[51] Int. Cl.[4] ............................................. G01N 15/06
[52] U.S. Cl. ..................................... 73/61 R; 73/599
[58] Field of Search ........................... 73/61 R, 19, 599

[56] References Cited

U.S. PATENT DOCUMENTS

| 2,966,056 | 12/1960 | Heller | 73/599 |
|---|---|---|---|
| 3,973,152 | 8/1976 | Karplus . | |
| 4,008,455 | 2/1977 | Pedersen . | |
| 4,009,616 | 3/1977 | Wonn . | |
| 4,020,693 | 5/1977 | Ahlgren et al. . | |
| 4,056,434 | 11/1977 | Barnes et al. . | |
| 4,112,735 | 9/1978 | McKnight . | |
| 4,391,149 | 7/1983 | Herzl | 73/861.25 |
| 4,412,451 | 11/1983 | Uusitalo et al. | 73/61 R X |

OTHER PUBLICATIONS

Claytor, T. N., *Void/Particulate Monitor Tests at EBR-II*, in Argonne Nat. Lab., publication ANL-8-2-60, pp. 1-16, Oct. 1982.
Miller, D. L., *Ultrasonic Detection of Resonant Cavitation Bubbles in a Flow Tube by their Second-Harmonic Emissions*, in Ultrasonics, pp. 217-224, Sep. 1981.

*Primary Examiner*—Stewart J. Levy
*Assistant Examiner*—Joseph W. Roskos
*Attorney, Agent, or Firm*—Jeannette M. Walder; Paul A. Gottlieb; Judson R. Hightower

[57] ABSTRACT

Voids and particulates are detected in a flowing stream of fluid contained in a pipe by a detector which includes three transducers spaced about the pipe. A first transducer at a first location on the pipe transmits an ultrasonic signal into the stream. A second transducer detects the through-transmission of the signal at a second location and a third transducer at a third location upstream from the first location detects the back-scattering of the signal from any voids or particulates. To differentiate between voids and particulates a fourth transducer is positioned at a fourth location which is also upstream from the first location. The back-scattered signals are normalized with the through-transmission signal to minimize temperature fluctuations.

16 Claims, 5 Drawing Figures

VOID/PARTICULATE DETECTOR

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

This invention relates generally to the detection of voids and particulates in a flowing stream of fluid.

The detection of voids and particulates in a flowing stream of fluid is of interest in several industries. For example, the detection of small particulates in photoresist is important for the semiconductor industry. Although these fluids are filtered, contaminants may be dislodged from walls by shock or other means. Impurity monitoring is needed to determine the cleanliness of storage tanks. In the medical arts it would be useful to monitor fluids pumped outside the body such as in a kidney dialysis machine. In the metals industry, small particles of oxides and gas bubbles in molten streams must be monitored to improve quality control.

The invention is particularly useful for detecting voids and particulates in the liquid metal coolant (sodium) of a fast breeder reactor. Although sodium has many advantages as a coolant, it is difficult to work with. It is reactive chemically and must be kept dry at all times. When water from the water-sodium heat exchanger leaks into the sodium, the resultant reaction produces hydrogen bubbles and sodium oxide particles. The principle prior art leak detection technique detects the presence of hydrogen dissolved in the sodium. Hydrogen is detected by the diffusion of hydrogen through a nickel membrane. Although the sensitivity of this technique is good, the response time is slow and the technique does not distinguish leak hydrogen from extraneous hydrogen which may be present in the system after tube cleaning and during initial operation. Also, since both particulates and gas bubbles are generated by a leak, a detector which detects both particulates and voids will enhance leak detection reliability.

Various acoustic techniques are also available, but are sensitive to background noise level changes from temperature fluctuations, which affect the transducer output.

Therefore, it is an object of the present invention to provide a method and apparatus for detecting voids and particulates in a flowing stream of fluid.

It is also an object of the present invention to provide a method and apparatus which distinguishes voids from particulates in a flowing stream of fluid.

It is another object of the present invention to provide a method and apparatus for detecting voids and particulates which are insensitive to temperature fluctuations.

It is yet another object of the present invention to provide a method and apparatus for detecting leaks in the liquid sodium coolant of a breeder reactor.

Additional objects, advantages and novel features of the invention will be set forth in part in the description which follows, and in part will become apparent to those skilled in the art by practice of the invention.

SUMMARY OF THE INVENTION

To achieve the foregoing and other objects and in accordance with the purposes of the present invention, a method of detecting voids and particulates in a flowing stream of fluid contained in a pipe may comprise: (a) transmitting an ultrasonic signal into the stream at a first location along the pipe; (b) detecting the through-transmission of said signal at a second location along the pipe; (c) detecting the back-scattering of said signal at a third location along said pipe, upstream from said first location; and (d) normalizing the backscattered signal to the through-transmitted signal, which normalized signal is a measure of the voids and particulates flowing past said first location. In order to differentiate between voids and particulates, the method may further comprise: (e) detecting the back-scattering of said signal at a fourth location along said pipe, upstream from said first location; and (f) normalizing the back-scattered signal at the fourth location to the through-transmitted signal, which second normalized signal is a measure of the voids flowing past said first location. Clearly, the two normalized signals can be substracted to determine a measure of the particulates flowing past said first location. Preferably, the second location is 180° from the first location as measured radially about the pipe and the third location is slightly upstream and in line with the first location. If only voids are to be detected, the third location should be slightly upstream from the first location and in line with the second location. Preferably, the fourth location is 90° from the third location as measured radially about the pipe (in either direction).

Apparatus for detecting voids and particulates in a flowing stream of fluid contained in a pipe may comprise: (a) a transducer for transmitting an ultrasonic signal into the stream, coupled to the pipe at a first location; (b) a second transducer for detecting the through-transmission of said signal, coupled to the pipe at a second location; (c) a third transducer for detecting the back-scattering of said signal, coupled to the pipe at a third location, said third location being upstream from said first location; (d) circuit means for normalizing the back-scattered signal from said third transducer to the through-transmitted signal from said second transducer; which normalized signal provides a measure of the voids and particulates flowing past said first location. In order to differentiate between voids and particulates, the apparatus may further include: (e) a fourth transducer for detecting the back-scattering of said signal, coupled to the pipe at a fourth location, said fourth location being upstream from said first location; and (f) second circuit means for normalizing the back-scattered signal from said fourth transducer to the through-transmitted signal from said second transducer; which second normalized signal provides a measure of the voids flowing past said first location.

BRIEF DESCRIPTION OF THE DRAWINGS

The present invention is illustrated in the accompanying drawings wherein.

DETAILED DESCRIPTION OF THE INVENTION

Figure 1:
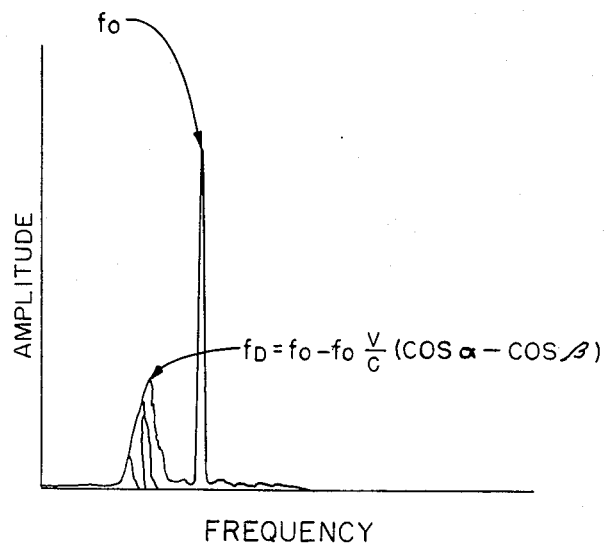
FIG. 1 shows the relationship between the frequency spectrum and the incident and back-scattered angles.

The void/particulate detector uses the principle of Doppler shift with a few modifications. A high frequency ultrasonic wave at a single frequency is transmitted by an ultrasonic transducer into a flowing fluid. Any obstruction, particle or void, that has an acoustic impedance different from that of the fluid, will reflect some of the ultrasonic energy backwards. Due to the Doppler effect, the back-scattered wave will be of lower frequency than the incident wave if the obstruction is moving away from the transmitting transducer. When obstructions pass the transducer there will exist in the scattered frequency spectra a peak centered at $f_d$, where $f_d = f_o - f_o\, v/c\, (\cos \alpha + \cos \beta)$. The Doppler frequency $f_d$ depends on the angle of transmission, $\alpha$, and the angle of scattering, $\beta$, as well as the sound velocity, c, in the fluid, the speed of the obstruction, v, and the frequency of the incident wave, fo. The relationship between fo and $f_d$ is shown in FIG. 1.

Figure 2:
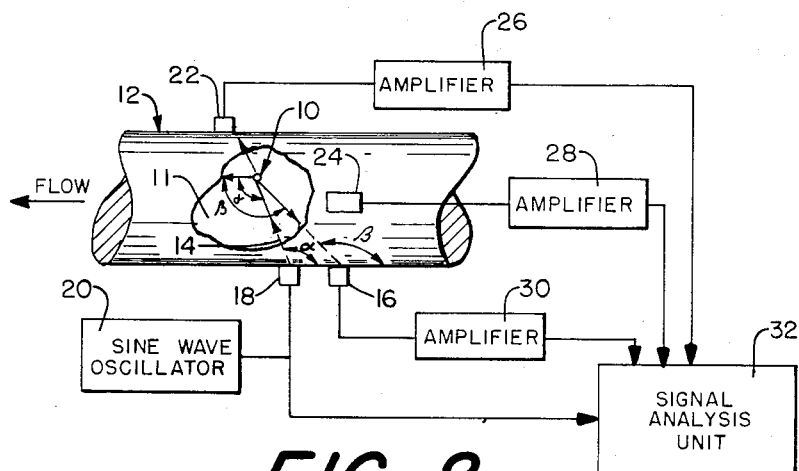
FIG. 2 is a schematic of the present invention showing an arrangement of four transducers on a pipe.

Referring to FIG. 2, obstruction 10, which may be either a void (bubble) or a particle is flowing in the direction shown down pipe 12. Signal source 20 (sine wave oscillator) inputs a signal to transducer 18 which converts the signal to an ultrasonic wave 14 directed into the fluid 11 at an angle $\alpha$, measured with respect to the direction of flow. The incident wave is partially reflected by obstruction 10 backwards to transducer 16, which generates a back-scattered signal in response thereto which is amplified by amplifier 30 before inputting to signal analysis unit 32. Transducer 22 is mounted across from transducer 18, 180° as measured about the pipe and slightly downstream of transducer 18 and detects the through-transmission portion of incident wave 14 and generates a through-transmission signal in response thereto, which is amplified by amplifier 26 before inputting to signal analysis unit 32.

To detect the difference between particulates and voids the transducers receiving the back-scattered wave must be oriented at different angles with respect to the transmitting transducer. The pressure distribution of a scattered wave from a particle or void is given by $$P \sim k^2 a^3 \left( \frac{K_e - K}{K} + \frac{3\rho_e - 3}{2\rho_e + \rho} \cos \theta \right) \quad (1)$$

for the long wavelength limit. In the equation, k is the wave vector $2\pi/\lambda$, a is the particle radius, $K_e$ is the compressibility of the particle, K is the compressibility of the fluid, $\sigma_e$ and $\sigma$ are the density of the particle and fluid respectively, and $\theta$ is the angle of scattering. For a solid particle $K \gg K_e$ and $\sigma_e > \sigma$, thus the equation reduces to $$P \sim (-1 + 3/2 \cos \theta). \quad (2)$$

Five times as much pressure is radiated in the backward direction, $\theta = \pi$ than in the forward direction. If the scattering particle is a bubble then $K_e \gg K$ and $\sigma \gg \sigma_e$. The equation reduces to $$P \sim \left(\frac{K_e}{K} - 3 \cos \theta\right), \quad (3)$$

however, $K_e/K$ is much larger than 3 cos $\theta$ so there is no dependence on angle.

Figure 2A:
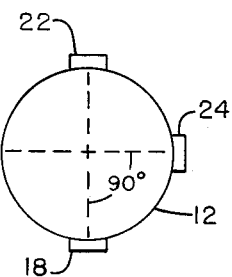
FIG. 2A is a cross-section of pipe 11 in FIG. 2 showing the radial placement of the transducers.

Referring again to FIG. 2 and FIG. 2A, transducer 24 is mounted on the pipe upstream from transducer 18 and rotated about the pipe at least 90° (in either direction) from transducer 16. Transducer 16 is mounted upstream of and as close to transducer 18 as possible, to receive the directly back-scattered wave. Thus, from equations (2) and (3), it can be seen that transducer 16 receives signals from both particulates and voids, while transducer 24 receives signals primarily from voids. Transducer 22 is used to normalize the signals received from transducers 24 and 16 so as to compensate for temperature variations. It should be noted that for good discrimination, transducer 24 must be placed at least 90° from transducer 16, as measured around the pipe (in either direction). If it is desired to measure only voids, transducer 16 may be eliminated and transducer 24 placed 180° (across a pipe diameter) and slightly upstream from transducer 18. For maximum discrimination between voids and particulates, transducer 24 should be 90° from transducer 16.

The void/particulate detector works because particles and gas bubbles usually have a different acoustic impedance than the fluid that they contaminate. The selection of the frequency of operation of oscillator 20 depends on the size of the particles or voids to be detected and the pipe thickness, diameter and material. In general, a frequency in the range of 5–15 MHz can be used to detect voids or particles down to 10 $\mu$m in diameter in pipes 30 cm in diameter. The technique disclosed is capable of measuring void fractions down to $10^{-11}$ and particle fractions of $10^{-7}$ making this technique very useful for impurity monitoring due to the high sensitivity.

Figure 3:
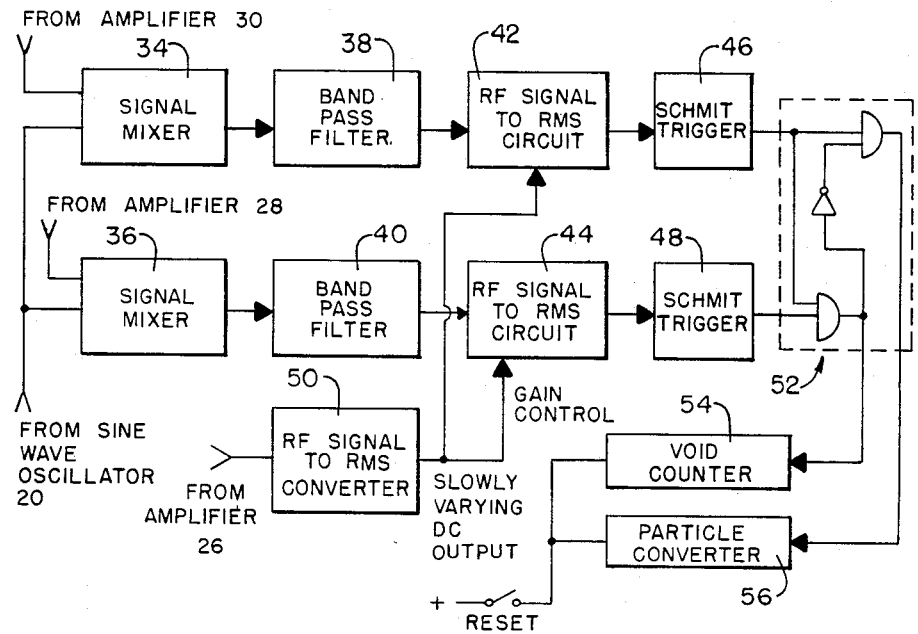
FIG. 3 is a block diagram of signal analysis unit 32 in FIG. 1.

Referring to FIG. 3 the outputs from amplifiers 30 and 28 are input with the output from oscillator 20 in mixers 34 and 36, respectively, which produce signal outputs $$f_L = f_o \pm f_{in} + \text{higher order harmonics}, \quad (4)$$

where $f_o$ is the frequency of the sine wave oscillator 20 and $f_{in}$ the frequency from amplifier 28 or 30. Usually if $f_o$ is 5 MHz then $f_L$ will be in the range of 100–5000 Hz. The outputs from mixers 34 and 36 are then input to band pass filters 38 and 40, respectively, which eliminate the higher frequency components that are of no interest.

Figure 4:
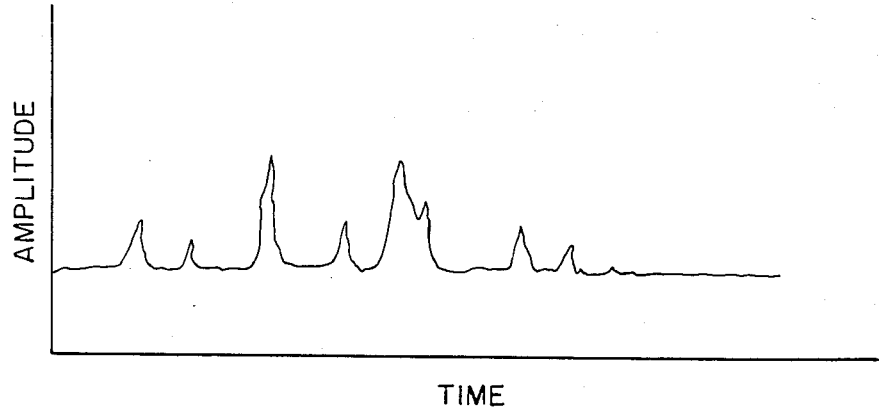
FIG. 4 is a diagram of a typical signal versus time curve at the output of converter 42, 44, or 50 in FIG. 3.

The through-transmission signal from amplifier 26 is rectified by converter 50 before being ratioed with the outputs of filters 38 and 40 in rms convertors 42 and 44, respectively. As stated before the signal from converter 50 is used to eliminate temperature fluctuations in the Doppler signals. FIG. 4 is an example of the time domain signal expected from the output of rms converters 42 and 44. These signals can be used to indicate the presence of voids and particulates (output of 42) or of voids only output of (44). Schmitt triggers 46 and 48 are used to convert the fluctuating rms signals from 42 and 44, respectively, to digital form. Logic circuit 52 is used to determine if obstruction 10 is a particle or a void. The counts are totalled in void counter 54 and particle counter 56.

The transducers used may be longitudinal or transverse wave wedge transducers mounted directly on the pipe, such as those described in U.S. Pat. No. 3,973,152 to Karplus. The main difference in the wedge transducers used here is the wedge angle. Transducers 18 and 22 are cut for 22° and transducers 16 and 24 are cut for 54°. The high temperature ultrasonic transducers installed on EBR-11 (Experimental Breeder Reactor II) in the configuration shown in FIG. 2 used lithium niobate crystals cut for the longitudinal mode. The transducer wedge, side plates, pressure point, and clamping block are made of 304 stainless steel. The clamp straps are made of Croloy (same material as the pipe) to minimize pressure changes in the transducer due to thermal expansion. The transducer wedge is coupled to the pipe with a 0.025 mm annealed gold foil. With the selection of wedge angles of 22° and 54°, in equation (1) $\alpha = 110°$ and $\beta = 120°$. The angle were chosen as close to optimum as practical given the engineering constraints. The void/particulate detector on EBR-II uses high temperature transducers and no stand-offs. Low temperature transducers with stand-offs were contemplated, but not chosen due to the sound attenuation in the stand-offs and temperature fluctuation problems.

The embodiments of this invention in which an exclusive property or privilege is claimed are defined as follows:

1. A method of detecting voids and particulates in a flowing stream of fluid contained in a pipe comprising:
   (a) transmitting an ultrasonic signal into the stream at a first location along the pipe;
   (b) detecting the through-transmission of said signal at a second location along the pipe;
   (c) detecting the back-scattering of said signal at a third location along said pipe, upstream from said first location, and
   (d) normalizing the back-scattered signal to the through-transmitted signal, which normalized signal is a measure of the voids and particulates flowing past said first location.

2. The method of claim 1 wherein said second location is 180° from said first location as measured radially about the pipe and said third location is slightly upstream and in line with said first location.

3. The method of claim 1 further comprising:
   (e) converting said normalized signal to a digital signal, whereby said digital signal is a measure of the number of voids and particulates flowing past said first location.

4. The method of claim 1 further comprising:
   (e) detecting the back-scattering of said signal at a fourth location along said pipe, upstream from said first location; and
   (f) normalizing the back-scattered signal at the fourth location to the through-transmitted signal, which second normalized signal is a measure of the voids flowing past said first location.

5. The method of claim 4 wherein said second location is 180° from said first location as measured radially about the pipe, said third location is slightly upstream and in line with said first location, and said fourth location is slightly upstream from said first location and at least 90° from said third location as measured radially about the pipe.

6. The method of claim 5 further comprising:
   (g) converting said normalized signal and said second normalized signal to digital and second digital signals, respectively;
   (h) subtracting said second digital signal from said digital signal to generate a third digital signal;
   whereby said second digital signal is a measure of the number of voids flowing past said first location and said third digital signal is a measure of the number of particulates flowing past said first location.

7. Apparatus for detecting voids and particulates in a flowing stream of fluid contained in a pipe comprising:
   (a) a transducer for transmitting an ultrasonic signal into the stream, coupled to the pipe at a first location;
   (b) a second transducer for detecting the through-transmission of said signal, coupled to the pipe at a second location;
   (c) a third transducer for detecting the back-scattering of said signal, coupled to the pipe at a third location, said third location being upstream from said first location; and
   (d) circuit means for normalizing the back-scattered signal from said third transducer to the through-transmitted signal from said second transducer, which normalized signal provides a measure of the voids and particulates flowing past said first location.

8. The apparatus of claim 7 further comprising:
   (e) a fourth transducer for detecting the back-scattering of said signal, coupled to the pipe at a fourth location, said fourth location being upstream from said first location;
   (f) second circuit means for normalizing the back-scattered signal from said fourth transducer to the through-transmitted signal from said second transducer,
   which normalized second signal provides a measure of the voids flowing past said first location.

9. The apparatus of claim 8 wherein said second location is 180° from said first location as measured radially about the pipe, said third location is slightly upstream and in line with said first location, and said fourth location is slightly upstream from said first location and at least 90° from said third location as measured radially about the pipe.

10. The apparatus of claim 7 wherein said second location is 180° from said first location as measured radially about the pipe and said third location is slightly upstream and in line with said first location.

11. The apparatus of claim 10 wherein said third location is slightly upstream of said first location and in line with said second location.

12. The apparatus of claim 9 further comprising:
   (g) digital circuit means responsive to said normalized and normalized second signals for generating digital signals indicative of the number of voids and particulates, respectively, in the stream.

13. The apparatus of claim 9 wherein said fourth location is 90° from said third location as measured radially about the pipe.

14. The apparatus of claim 13 wherein said transducers are longitudinal wave wedge transducers mounted externally to the pipe.

15. The apparatus of claim 13 wherein said first and second transducers have wedge angles of 22° and said third and fourth transducers have wedge angles of 54°.

16. The apparatus of claim 13 wherein said transducers are transverse wave wedge transducers mounted to the pipe.

* * * * *